United States Patent
Österlind et al.

[11] Patent Number: 5,957,887
[45] Date of Patent: Sep. 28, 1999

[54] INFUSION CATHETER ASSEMBLY NEEDLE PROTECTION DEVICE

[75] Inventors: Roland J. Österlind, Hoeganaes; Lars A. Lindgren; Hans A. Nilsson, both of Helsingborg, all of Sweden

[73] Assignee: Becton Dickinson Infusion Therapy Aktiebolag, Helsingborg, Sweden

[21] Appl. No.: 08/911,202

[22] Filed: Aug. 14, 1997

[30] Foreign Application Priority Data

Aug. 21, 1996 [GB] United Kingdom ................ 96175021

[51] Int. Cl.⁶ .................................................. A61M 5/00
[52] U.S. Cl. ......................... 604/110; 604/198; 604/164
[58] Field of Search ................................. 604/110, 263, 604/192, 198, 195, 158, 162, 163, 164, 171

[56] References Cited

U.S. PATENT DOCUMENTS

| | | | |
|---|---|---|---|
| 4,978,343 | 12/1990 | Dysarz et al. | 604/198 |
| 5,129,884 | 7/1992 | Dysarz | 604/195 |
| 5,211,629 | 5/1993 | Pressly et al. | 604/195 |
| 5,295,963 | 3/1994 | Deeks | 604/198 |
| 5,651,772 | 7/1997 | Arnett | 604/198 |
| 5,702,367 | 12/1997 | Cover et al. | 604/198 |
| 5,807,352 | 9/1998 | Tamaro | 604/263 |

*Primary Examiner*—Ronald Stright
*Attorney, Agent, or Firm*—Eric M. Lee

[57] ABSTRACT

A medical catheter device that has a housing containing a needle and needle hub that are movable between a retracted position where the needle is safely within the protection of the housing and an extended position where the needle extends from the housing for insertion into a patient. After use, the needle can be moved to its retracted position to protect the user from inadvertent sticks from the needle. At the distal end of the catheter housing, there is a hub support having a through hole through which the needle extends when in its extended position. A flexible hollow trunk extends proximally from the through hole back into the housing and through which the needle passes. When the needle is withdrawn into its retracted position, the needle is physically caused to be moved off center so as to not realign with the through hole, however, the needle end remains encased within the flexible hollow trunk to prevent blood from entering the through hole into the interior of the housing.

4 Claims, 2 Drawing Sheets

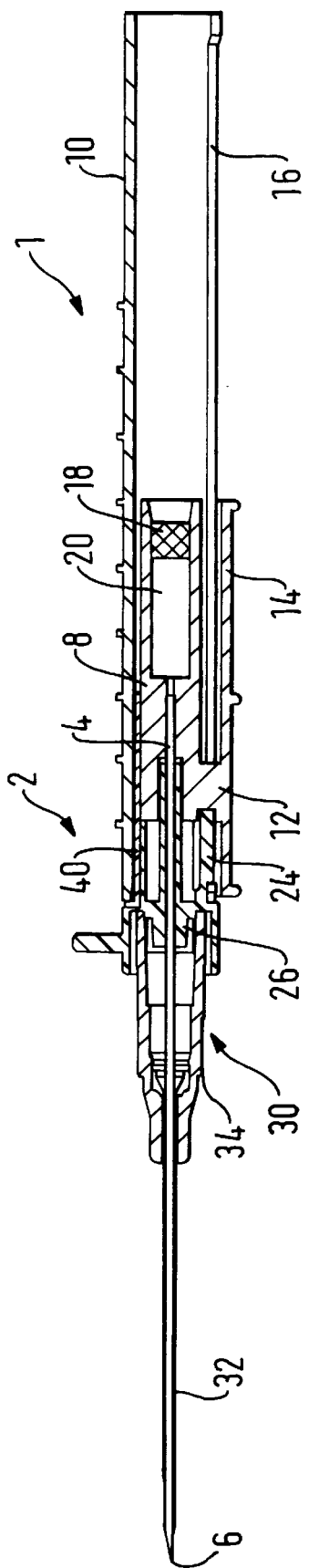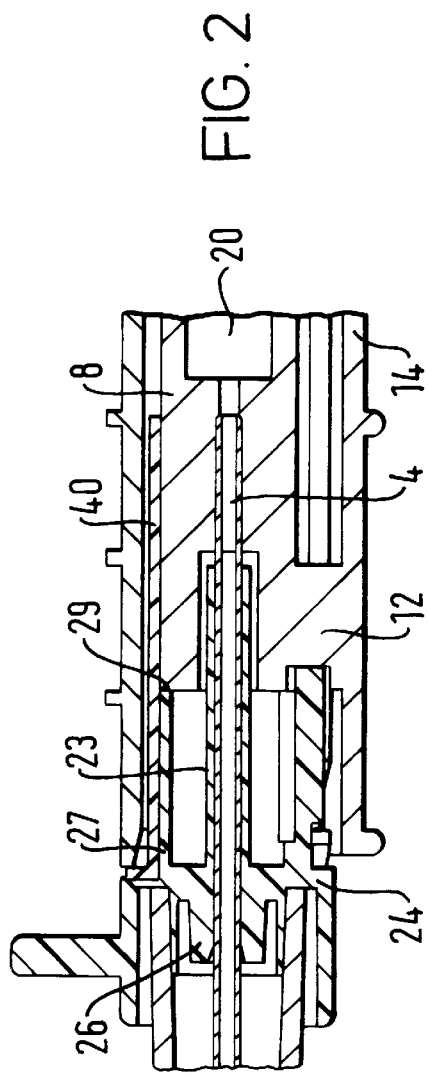

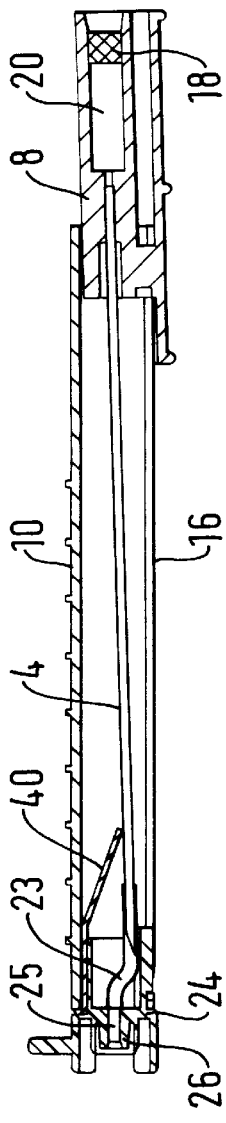
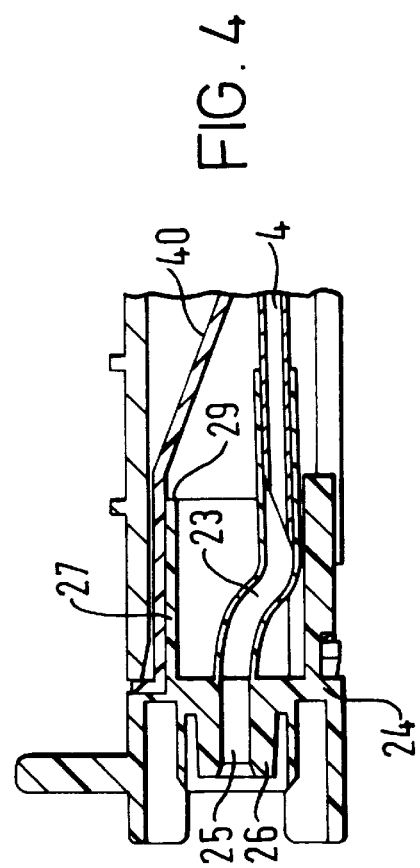
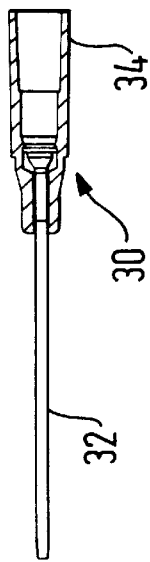

INFUSION CATHETER ASSEMBLY NEEDLE PROTECTION DEVICE

The present invention relates to medical devices and in particular, to medical devices such as intravenous catheters, which include a hollow needle having a sharp distal end or tip for piercing the skin of a patient.

BACKGROUND OF THE INVENTION

The existence of infectious diseases such as AIDS and hepatitis has highlighted the danger to which medical personnel may be exposed when treating patients by means of catheter devices where a sharp needle tip is used to pierce the skin of a patient. Medical personnel have been infected by physical contact with, or accidental prick by an infected needle (needle-stick).

In order to protect medical personnel against inadvertent needle-stick, a number of solutions have been developed whereby a protective means incorporated within the catheter prevents physical contact with the needle after use and hence against inadvertent needle-stick.

One known device for protecting the needle after use is described in European Patent 5447501. In this document, there is described an infusion catheter assembly including a hollow needle having a sharpened distal tip for piercing the skin of a patient. In a ready-for-use position the needle passes through a hole in a rigid front part which houses a resilient member.

The resilient member is retained under tension by the needle flank and exerts a force substantially at right angles to the longitudinal direction of the needle. In its retracted position, that is, when the needle tip is moved back through and beyond the hole in the rigid front part and within a main housing, the resilient member biases the needle tip laterally to prevent reentry of the needle tip through the hole.

This device is a relatively simple and economic device and is effective to minimise the danger of inadvertent needle stick. However, a disadvantage of this known device is that once the needle tip is moved back through and beyond the hole in the rigid front part there is nothing to prevent blood from flowing through the hole and into the housing.

It is an aim of the present invention to provide means for protecting the tip of a needle forming part of a medical device which includes means for preventing or inhibiting the flow of blood into the needle protection means.

SUMMARY OF THE INVENTION

According to the present invention, a medical device comprises a hollow needle having a sharpened distal tip for piercing the skin of a patient, means for moving the needle relative to a hub support member between a first ready-for-use position and a second retracted needle protected position, the hub support member being formed with a through hole for the passage therethrough of the needle and resilient means which, in the second retracted needle protected position, engages the needle to prevent the needle tip passing back through the hole, characterised in that a flexible hollow trunk extends rearward of the hub support member the hollow interior of which is aligned with the through hole and through which the needle extends in its ready-for-use position.

Preferably, the resilient means is in the form of a resilient arm having a free end which in the second retracted needle protected position of the needle, engage the needle flank to move the needle tip and the trunk laterally, thereby to prevent the needle tip re-entering the hole.

BRIEF DESCRIPTION OF THE DRAWINGS

An embodiment of the invention will now be described, by way of example, reference being made to the FIGS. of the accompanying diagrammatic drawings in which:

FIG. 1 is a longitudinal cross-section through an infusion catheter assembly with its needle in a ready-for penetration position;

FIG. 2 is an enlarged detail of the catheter assembly of FIG. 1;

FIG. 3 is a longitudinal cross-section similar to FIG. 1 but showing the needle in its needle protected position; and FIG. 4 is an enlarged detail of the catheter assembly of FIG. 3.

DETAILED DESCRIPTION OF THE INVENTION

As shown, an infusion catheter assembly 1 includes a needle assembly 2 comprising a hollow needle 4 having a sharpened distal tip 6, said needle 4 extending forwardly from a needle hub 8. The needle hub 8 is located for sliding movement within a housing 10 and includes a lug 12 supporting a gripper 14. The lug 12 extends through a slot 16 formed in the housing 10 in order that the gripper 14 can be engaged to reciprocate the needle hub 8 forwardly and rearwardly along the length of the housing 10. The needle hub 8 is hollow and is closed by a filter 18 which with the hub 8 defines a blood flash back chamber 20.

The forward distal end of the housing 10 is effectively closed by a hub support member 24 connected thereto. Extending rearwardly from the hub support member 24 is a flexible hollow tubular trunk 23. The hollow interior of the trunk 23 is aligned with a through passage 25 in the hub support member 24 to allow the passage therethrough of the needle 4. A shroud 27 also extends rearwardly from the hub support member 24 and has a proximal free end 29. The forward face of the member 24 is formed with a forwardly extending boss 26 for the support of the proximal end of a cannula assembly 30. As is well known in the art, the cannula assembly 30 comprises a hollow cannula 32 attached to a cannula hub 34.

A resilient arm 40 is mounted between the hub support member 24 and the housing 10 and extends rearwardly (as shown) between an inside surface of the housing 10, the outer surface of shroud 27 and a surface on the needle hub 8.

In the ready-for-use position as illustrated in FIGS. 1 and 2, the needle hub 8 is located at the forward end of the housing 10 abutting the proximal free end 29 of the shroud 27. In this position, the needle 4 extends through the hollow trunk 23 and the hole 25 in the hub support member 24 and through the cannula assembly 30 so that its distal tip 6 extends beyond the free distal end of the hollow cannula 32.

Once penetration of the patient's skin has been effected, the gripper 14 is engaged to move the needle hub 8 rearwardly towards the proximal end of the housing 10, that is, towards the position illustrated in FIG. 3. This movement of the needle hub 8 will cause the needle 4 to be withdrawn through the hollow cannula 32, the cannula hub 34, and the hole 25 in the hub support member 24. At the same time as the needle hub 8 clears the proximal free end of the arm 40, said arm 40 will press downwardly (as shown) against the flank of the needle 4 thereby causing it to be deflected laterally out of alignment with the hole 25. The trunk 23 being flexible will follow the movement of the distal end tip 6 of the needle 4.

In this position, the cannula assembly 30 can now be removed from the boss 26 of the hub support member 24.

A particular advantage of the embodiment described above is that the needle 4 within the hollow trunk 23 effectively prevents or inhibits the flow of blood into the housing 10. Even if the tip 6 of the needle 4 pierces the trunk 23 it will still act to block the flow of blood into the housing 10.

It will be appreciated that although a resilient cantilever arm 40 has been described to effect lateral movement of the needle 4 after the needle tip 6 has cleared the passage 25 in the hub support member 24 in fact any resilient member could be used as, for example, describe in European Patent 5447501.

Furthermore, the hub support member 24 and the trunk 23 can be moulded as an integral item for cheapness of manufacture.

We claim:

1. A medical device, comprising:

a needle having a proximal end and a sharp distal tip for piercing the skin of a patient;

a needle hub connected to said proximal end of said needle;

a housing having a distal end, a hub support mounted to said distal end of said housing and having an through hole for the passage of said needle, said needle hub and said needle being slidably disposed in said housing between a retracted position wherein said needle is contained within said housing and an extended position wherein said needle extends outwardly from said distal end of said housing through said through hole;

a flexible hollow trunk extending proximally from said through hole within said housing wherein said needle passes through said flexible hollow trunk when said needle is in said extended position and said sharp distal tip of said needle remains within said flexible hollow trunk when said needle is in said retracted position; and means to engage said needle to move said needle out of alignment with said through hole when said needle is moved to said retracted position.

2. A medical device as defined in claim 1 wherein said means to engage said needle comprises a resilient arm that provides a force on said needle to move said needle.

3. A medical device as defined in claim 2 wherein said resilient arm is located within said housing and extends proximally from said hub support member.

4. A medial device as defined in claim 1 wherein said hub support member and said trunk are integrally molded together.

* * * * *